United States Patent [19]

Kawashima et al.

[11] Patent Number: 4,740,747
[45] Date of Patent: Apr. 26, 1988

[54] METHOD OF AND APPARATUS FOR MEASURING TRANSFORMATION DEGREE

[75] Inventors: Katsuhiro Kawashima; Masaaki Hatta; Hiroshi Yada, all of Kitakyushu, Japan

[73] Assignee: Nippon Steel Corporation, Tokyo, Japan

[21] Appl. No.: 705,467

[22] PCT Filed: Jun. 14, 1984

[86] PCT No.: PCT/JP84/00309
§ 371 Date: Feb. 11, 1985
§ 102(e) Date: Feb. 11, 1985

[87] PCT Pub. No.: WO85/00058
PCT Pub. Date: Jan. 3, 1985

[30] Foreign Application Priority Data

Jun. 15, 1983 [JP]  Japan ................ 58-107313
Jun. 15, 1983 [JP]  Japan ................ 58-107314
Jun. 15, 1983 [JP]  Japan ................ 58-107315

[51] Int. Cl.⁴ ......................................... G01N 27/80
[52] U.S. Cl. ................................. 324/239; 324/203; 324/236

[58] Field of Search ............... 324/203, 228, 234, 236, 324/237, 238, 239, 241, 242, 243; 338/84 M

[56] References Cited

U.S. PATENT DOCUMENTS 2,933,677  4/1960  Lieber ................. 336/84 M
3,247,453  4/1966  Quittner ............... 324/241
4,059,795  10/1977 Mordwinkin .......... 324/233
4,105,971  8/1978  Nevalainen ........... 324/203

FOREIGN PATENT DOCUMENTS

2486661  1/1982  France ................ 324/203

Primary Examiner—Gerard R. Strecker
Assistant Examiner—Robert W. Mueller
Attorney, Agent, or Firm—Pollock, Vande Sande & Priddy

[57] ABSTRACT

A method of and apparatus for measuring the degree of transformation of the structure of an object. An object is placed between a transmission coil and a receiving coil. An A.C. current or a pulse current or a combination of the A.C. current and the pulse current are supplied to the transmission coil, and the degree of transformation is detected by means of an electric signal obtained through the receiving coil.

5 Claims, 8 Drawing Sheets

FIG. 7a 
WAVEFORM OF TRANSMITTED SIGNAL

FIG. 7b 
TRANSFORMATION DEGREE 0%

FIG. 7d 
TRANSFORMATION DEGREE 20%

FIG. 7e 
TRANSFORMATION DEGREE 40%
OUTPUT×10

FIG. 7f 
TRANSFORMATION DEGREE 80%
OUTPUT×100

METHOD OF AND APPARATUS FOR MEASURING TRANSFORMATION DEGREE

TECHNICAL FIELD

The present invention relates to a method of and an apparatus for measuring degree of transformation of an object such as steel through detection of an electromagnetic change which occurs in the course of a crystalline transformation of the object from austenite to ferrite and vice versa.

BACKGROUND ART

Hitherto, various methods have been proposed for measuring transformation, such as a method making use of radioactive rays, method making use of D.C. magnetic field, and a method which relies upon detection of electromagnetic change caused in the course of transformation as a change in the coil impedance. The measuring method employing the radioactive rays makes use of such a phenomenon that the angle of X-ray diffraction changes due to change from austenite to ferrite. With this method, however, information is available only with the surface area of several tens of microns from the object surface, because of poor permeability of the X-rays in the object, and the measurement is too largely affected by fluttering of the object. The method making use of D.C. magnetic field employs a hole element for measuring the intensity of the D.C. magnetic field applied to the object. This method, however, suffers from a disadvantage in that there is a large non-linearity between the transformation degree and the measured value. In addition, this method permits the measurement of the transformation degree only in the period immediately after the commencement of the transformation because the magnetic field flows only through the surface region of the object when the object has come to exhibit ferromagnetic property.

Figure 1:
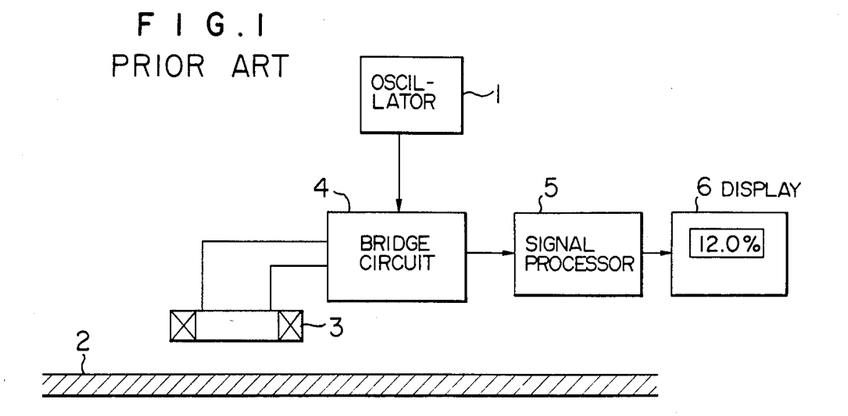
FIG. 1 is a block diagram showing the arrangement of a conventional transformation degree measuring apparatus.

A description will be made hereinunder as to the transformation degree measuring method relying upon the coil detection of electromagnetic change in the course of the transformation, because the method of the invention also basically relies upon this principle. FIG. 1 shows a system for carrying out this type of measuring method. This system includes an oscillator 1 for producing sine-wave electric current of an appropriate frequency. A detection coil 3 is placed in the close proximity of the upper side of an object 2 to be examined, so as to detect any change in the amount of transformation in the object 2. A reference numeral 4 designates a bridge circuit for detecting any change in the impedance of the detection coil 3, while numeral 5 designates a signal processor for processing the detection signal derived from the bridge circuit 4 into signals of a form easy to use. Numeral 6 denotes a display.

In the operation of this system, the detection coil 3 is placed in the close proximity of a tabular object 2 to be examined, and a continuous sine-wave current is applied to the detection coil from the oscillator 1. Consequently, eddy current is generated in the surface of the object 2, so that the impedance of the coil is changed seemingly.

The amplitude of the eddy current affecting the coil impedance depends on the properties of the object material and other factors, i.e., magnetic permeability, conductivity, distance between the sensor and the object and so forth. When the transformation of the object from austenite to ferrite is proceeding, the magnetic permeability is largely changed because the ratio of ferrite to austenite in the object is increased. Consequently, the amplitude of the eddy current in the surface region of the object is changed to cause a change in the impedance of the detection coil 3 placed in the vicinity of the object. This change in the impedance is detected by the bridge circuit 4 connected to the coil, so that the change in the impedance as an index of the amount of transformation is obtained through the signal processing by the signal processor 5 and displayed on the display 6.

This known system for measuring the transformation degree relying upon a detection coil is sensitive not only to the change in the magnetic permeability of the object but also to other factors, particularly to the distance between the object and the detection coil. It is, therefore, essential to keep a constant distance between the object and the detection coil. In addition, since there is a large non-linearity between the sensor output and the transformation degree it is not possible to measure the transformation degree over a wide range from the beginning to the end of the transformation, although the measurement can be made satisfactorily in a short period immediately after the commencement of transformation.

SUMMARY OF THE INVENTION

In view of the above, the present invention aims as its primary object at providing a transformation degree measuring method improved such as to obviate the above-described problems of the prior art.

To this end, according to the invention, the detection coil is divided into a transmission coil and a receiving coil which are disposed to oppose each other across the thickness of a tubular object thereby eliminating any influence of the fluctuation of the distance between the object and the sensor and allowing a measurement over the whole period from the beginning till the end of the transformation over a wide variety of thickness of the object.

Thus, according to one aspect of the invention, the transformation degree of an object is detected by using an A.C. current or pulse current applied to a transmitting coil with the object placed between the transmitting coil and a receiving coil which oppose the transmitting coil across the thickness of the object.

According to another aspect, A.C. current is used in the beginning period of the transformation and, after the transformation has proceeded to a predetermined degree, a pulse current is used in place of the A.C. current thereby ensuring the precision of measurement and to allow the measurement in the region where the measurement cannot be conducted with A.C. current.

According to still another aspect, the measurement of the transformation degree is conducted over the whole period from the beginning to the end of the transformation in specific relations to the magnetic permeability, conductivity and thickness of the object.

According to a further aspect, the transformation degree of the object is conducted by means of a transmission coil which receives signal current from a signal generator and a receiving coil which delivers an electric signal to a display through a signal processing unit.

As has been described, according to the invention, the amplitude of the signal received by the receiving coil is not changed substantially by the position of the object between the transmission and receiving coils which are arranged to oppose each other across the measuring object. That is, the fluctuation of the measured result due to fluttering of the object is effectively suppressed. In addition, the measurement can be conducted highly precisely over the whole period from the beginning to the end of the transformation by the use of continuous wave, pulse wave and combination of the pulse and continuous waves.

BRIEF DESCRIPTION OF THE DRAWINGS

FIGS. 6a to 6d show different examples of arrangement for avoiding the detouring phenomenon, wherein

FIGS. 7a to 7e are illustrations of waveforms of the transmitted pulses and received pulses in different states of transformation, wherein:

FIG. 7a shows the transmitted pulses;

FIG. 7c shows the waveform of received signal as observed when the transformation degree is 20%;

THE BEST MODE FOR CARRYING OUT THE INVENTION

Figure 2:
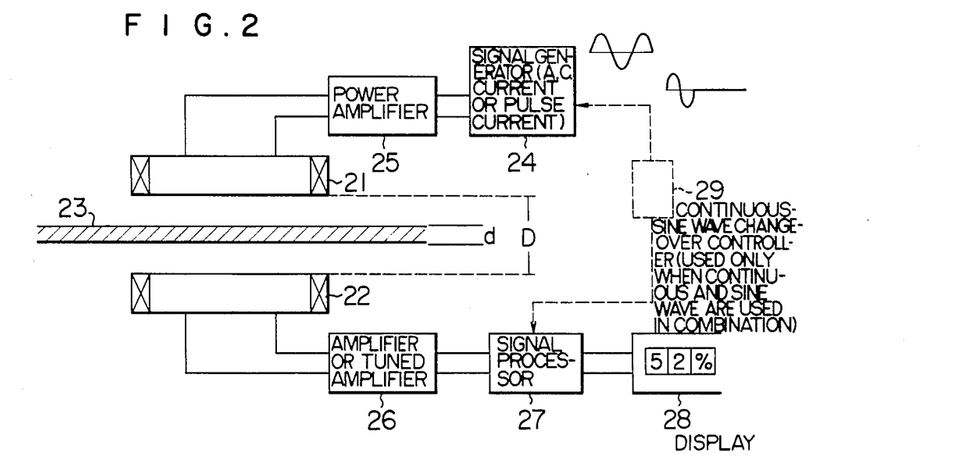
FIG. 2 is a block diagram showing the arrangement of a transformation measuring apparatus in accordance with the invention.

The invention will be described in detail hereinunder with reference to the drawings showing preferred embodiments of the invention. Referring to FIG. 2, a transformation degree measuring apparatus in accordance with the invention has a transmission coil 21 and a receiving coil 22. The receiving coil 22 is disposed to oppose the transmission coil 21 across the thickness of a tabular object 23 to be examined. A reference numeral 24 denotes a signal generator which is adapted to produce an electric current of a form suitable for the measurement of degree of transformation in the object, e.g., an A.C. current or a pulse current. A power amplifier 25 is adapted to impart a power to the high-frequency current, while an ordinary amplifier or a tuned amplifier 26 is adapted to amplify the voltage generated in the receiving coil. A reference numeral 27 denotes a signal processing circuit for processing the received signal. The signal processing circuit has a function to convert the received high-frequency current or pulse current to a predetermined transformation degree. The processed signal is displayed on a display 28. A pulse-continuous wave change-over switch 29 is used for selection or changing-over between pulse wave and continuous wave.

The operation of this apparatus is as follows.

When a sine-wave continuous electric current is supplied to the transmission coil 21, eddy currents are generated on the surface of the tabular object to be examined. The eddy currents propagate downwardly through the thickness of the object and a magnetic field of a high frequency around the receiving coil 22 is formed. Consequently, a voltage is induced between both terminals of the receiving coil 22.

It is well known that the voltage induced in the coil can be approximated by the following formula:

$$V = V_0 \exp(-\sqrt{\pi f \mu \sigma} d) \quad (1)$$

f: frequency, $\mu$: magnetic permeability, $\sigma$: conductivity, d: plate thickness As stated before, the austenite structure of the object is progressively changed into ferrite structure as the transformation proceeds, so that the magnetic permeability of the object is gradually increased in accordance with the increment of the ratio of ferrite structure to the total structure which is the sum of the austenite and ferrite structures.

Representing the ratio of ferrite structure to the total structure by K, and the magnetic permeabilities and the conductivities of the austenite and ferrite by $\mu_1$, $\mu_2$ and $\sigma_1$, $\sigma_2$, respectively, the voltage induced between both terminals of the receiving coil 22 is expressed by the following formula:

$$V = V_0 \exp(-\sqrt{\pi f \mu_1 \sigma_1}(1-K)d - \sqrt{\pi f \mu_2 \sigma_2 K d}) \quad (2)$$

$\mu_1$, $\mu_2$: magnetic permeabilities of austenite and ferrite
$\sigma_1$, $\sigma_2$: conductivities of austenite and ferrite
f: frequency
K: ferite/(austenite + ferrite)

The ratio K corresponds to the transformation degree. Values other than K are all known. It is, therefore, possible to determine the transformation degree K by measuring the voltage induced. Thus, the invention is based upon the principle expressed by the formula (2). It will be seen that the formula (2) includes no term which would relate to the distance between the sensor and the object, that is, the voltage induced is independent from the distance between the tabular object and the sensor and, hence, the transformation degree which is determined by the induced voltage is independent from the distance between the sensor and the tabular object.

For this reason, the invention permits a highly precise measurement of the transformation degree even when the object flutters during the measurement, as in the case of a strip mill in which the strip rolled by the mill winds and flutters vertically as it runs along the path.

The logarithmic conversion of the formula (2) shows, as will be seen from the following formula (3), that the logarithm of the induced voltage has a linear relation to the transformation degree K, because the magnetic permeability of ferrite is much greater than that of austenite:

$$l_n(V/V_0) = (-\sqrt{\pi f \mu_1 \sigma_1}(1-K)d + \sqrt{\pi f \mu_2 \sigma_2 Kd})$$

because of condition of $\mu_2 >> \mu_1$, $$l_n(V/V_0) = -\sqrt{\pi f \mu_2 \sigma_2 Kd} \quad (3)$$

From this fact, it will be understood that the measurement can be conducted uniformly over a wide range of transformation degree K.

Figure 3:
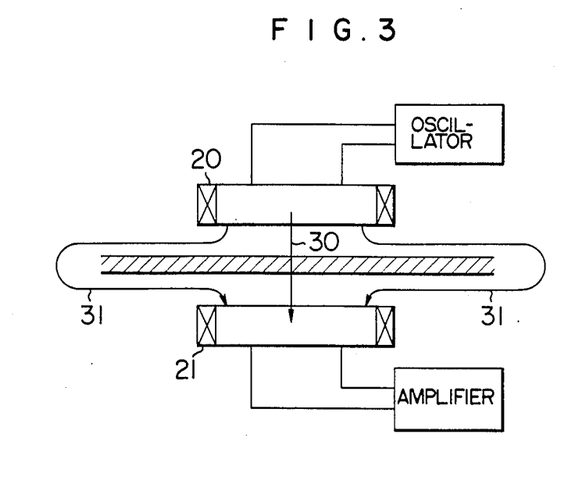
FIG. 3 is an illustration explanatory of a detouring of phenomenon.

As will be seen from formula (3), the induced voltage is a function of the transformation degree K and, in addition, depends on the thickness of the object. Therefore, when the object has a large thickness d, the voltage V induced by the transmitted signal 30 as shown in FIG. 3 is involved by a voltage $V_\epsilon$ which is produced by a signal 31 detouring the object, if the transformation has been proceeded sufficiently. In the case where the voltage produced by the detouring of the signal is not negligible, the following formula (4) applies in place of the formula (2):

$$V = V_0 \exp(-\sqrt{\pi f \mu_2 \sigma_2 Kd}) + V_\epsilon \quad (4)$$

Therefore, for determining the condition necessary for the prevention of detouring at 100% transformation, i.e., at the state of K=1, it is assumed that the following condition exists due to large value of Kd:

$$V_0 \exp(-\sqrt{\pi f \mu_2 \sigma_2 d}) = V_\epsilon$$

The frequency which meets this condition is represented by $f_\epsilon$. Assuming here frequencies f which is lower than 80% of the above-mentioned frequency $f_\epsilon$, i.e., $f < 0.8 f_\epsilon$, the following condition is established:

$$V_0 \exp(-\sqrt{\pi f \mu_2 \sigma_2 d}) >> V_\epsilon$$

Thus, when the frequency f is selected to meet the condition of $f \leq 0.8 f_\epsilon$, the condition approximately follows the formula (3) over the whole period from the beginning (K=0) till the end (K=1) of the transformation.

Therefore, the measurement can be conducted safely over the wide region from the beginning to the end of the transformation, if the following condition is met:

$$f \leq 0.8 f_\epsilon = \frac{K_0}{\mu \sigma d^2}$$

where, $$K_0 = \frac{0.8 (l_n (V_\epsilon/V_0))^2}{\pi}$$

$K_0$: a factor which is determined by condition of three-dimensional arrangement.

Figure 4A:
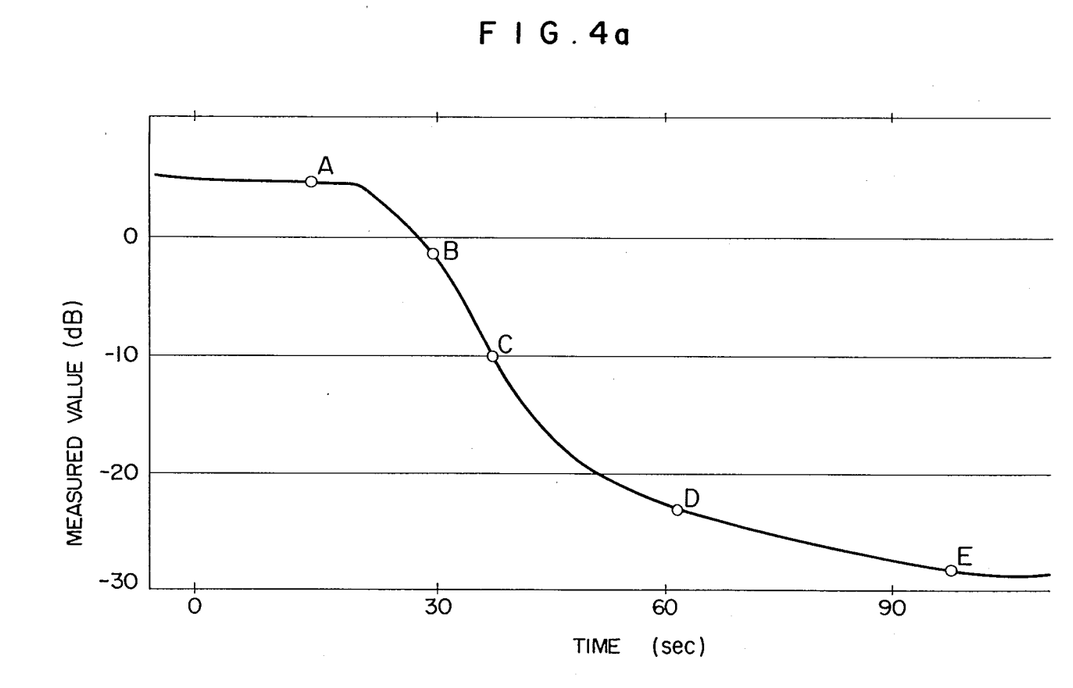
FIG. 4a is a graph showing measured values corresponding to the state as shown in FIG. 4b.
Figure 4B:
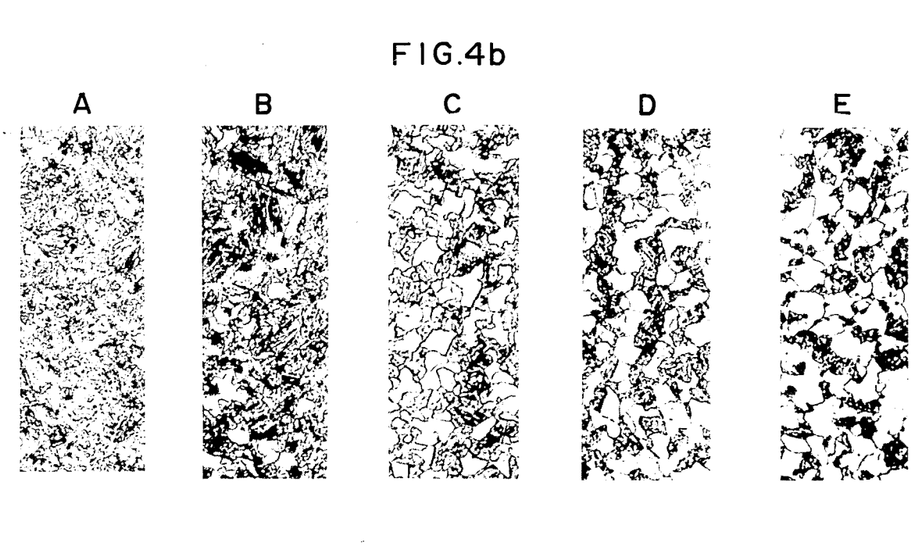
FIG. 4b is a photographic presentation of the state of proceed of the transformation in the object.

FIG. 4a shows the result of measurement in the batch condition in accordance with the method explained hereinbefore. The photographs in FIG. 4b show the structure in different stages of the transformation, corresponding to the values appearing in FIG. 4a showing the result of measurement. The regions shown by white blanks are the region where the ferrite is formed. It will be seen that the region of ferrite is gradually increased from the left (transformation degree 0%) to the right (transformation degree 80%), thus proving that the transformation is proceeding, followed by a corresponding reduction in the value obtained from the receiving coil.

The thus obtained measured value is converted by the signal processor 27 into transformation degree K in accordance with the formula (3), and the result is displayed on the display 28.

As will be understood from the foregoing description, the present invention permits a measurement with the highest degree of sensitivity over whole period from the beginning till the end of the transformation, provided that the oscillation frequency of the oscillator is suitably adjusted in accordance with the thickness of the object to be examined.

Figure 5:
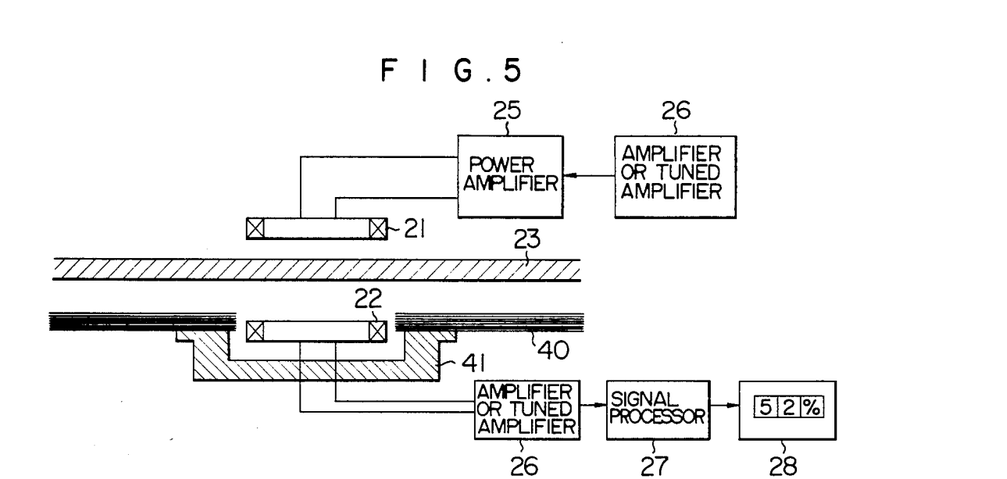
FIG. 5 is an illustration of a measuring system of the invention improved to avoid any detouring phenomenon.

In the described embodiment, it is necessary that the frequency to be used is rather low, when the object to be examined has a large thickness. The use of such a low frequency causes another problem that the sensitivity of the receiving coil to the signal to be received is reduced undesirably. FIG. 5 shows a basic system which is improved to obviate this problem.

Considering that the restriction of the frequency is made for the purpose of eliminating the influence of the detouring magnetic field, this basic system is arranged to minimize the magnetic field which reaches the receiving sensor while detouring the object. Namely, in this basic system, the receiving sensor is shielded by a shield plate 40 and a shield cup 41 made of a material having a large magnetic permeability and exposing only the portion of the receiving sensor facing the transmission sensor.

Figure 6A:
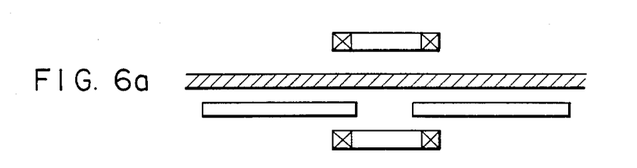
FIG. 6a shows an example in which the detouring phenomenon is avoided solely by a shield plate.
Figure 6B:
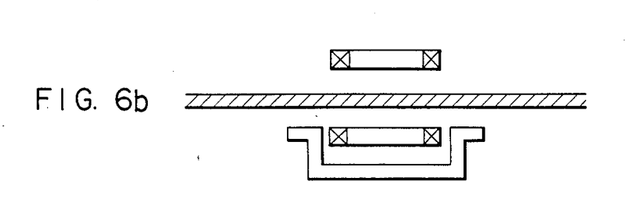
FIG. 6b shows an example in which the detouring phenomenon is avoided solely by a shield cup.
Figures 6C, 6D:
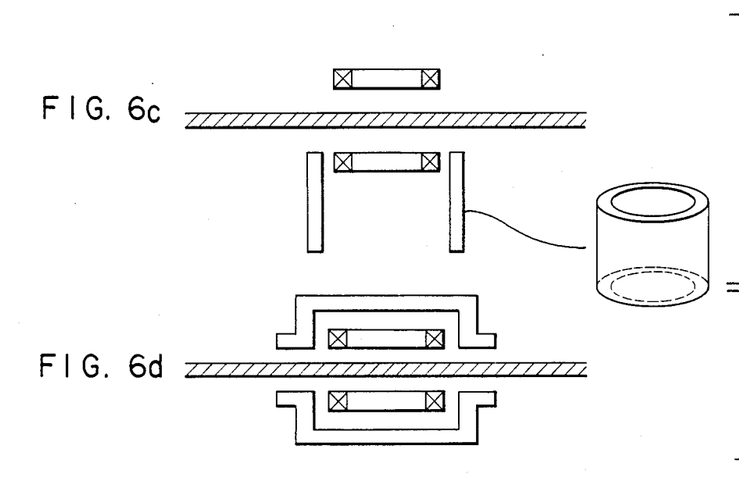
FIG. 6c shows an example in which the detouring function is avoided by a cylindrical tube.
FIG. 6d shows an example in which the detouring phenomenon is avoided by shield cups which surround the transmission and receiving coils.
Figure 7A:
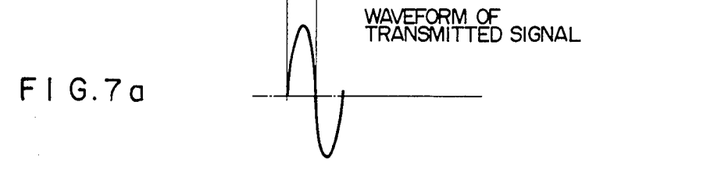
Figure 7B:
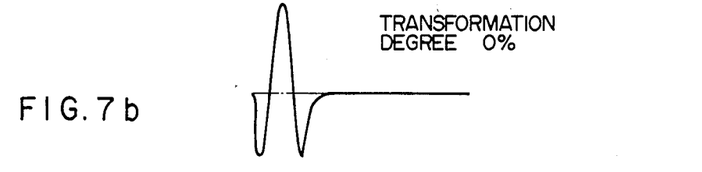
FIG. 7b shows the waveform of the received signal as observed when the transformation degree is 0%.
Figure 7D:
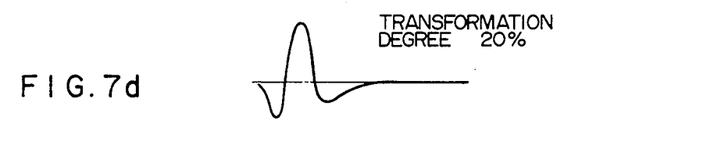
FIG. 7d shows waveforms of received signals observed when the transformation degree is 40%.
Figure 7E:
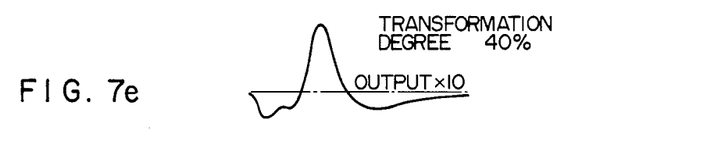
FIG. 7e shows the waveform of the received signal as observed when the transformation ratio is 80%.
Figure 7F:
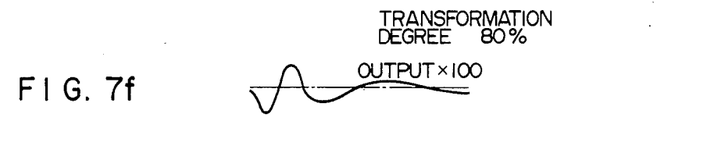

FIG. 6 shows various forms of the shield cup.

This improvement effectively increases the value of $K_0$ appearing in the formula (5), so that electric current of higher frequency can be put into use even for objects having a given thickness.

Although the basic system shown in FIG. 5 employs both the shield plate and the shield cup, it is not essential to use both of them simultaneously, and the shield plate and cup can be substituted by equivalent shielding means. For instance, FIG. 6a shows a modification in which a shield plate is used solely, FIG. 6b shows a modification in which a shield cup is used solely, FIG. 6c shows a modification in which a cylindrical tube having a high magnetic permeability is used in place of the shield cup, and FIG. 6d shows the case where both the transmission coil and the receiving coil are shielded by shield cups.

The embodiment described hereinbefore makes use of information in the form of a voltage induced in the receiving coil. This, however, is not exclusive and the information can be derived from the phase of the induced voltage. Namely, the information may be obtained in the form of the phase instead of the amplitude of the induced voltage.

Although in the described embodiment an electric current in the form of a continuous wave is used, the electric current supplied to the transmission coil may be a pulse current.

An explanation will be made as to the operation of the apparatus performed when the electric current in the form of pulses is used.

When a pulse wave current is supplied to the transmission coil 21, eddy currents are generated on the surface of the tabular object as is well known. These eddy currents are progressively propagated downwardly through the thickness of the object and forms a pulsating magnetic field around the receiving coil 22. As a result of pulsation of the magnetic field, a voltage is induced between both terminals of the coil 22.

It is assumed here that the pulse current I is given as follows:

$$I = I_0(t) \quad (nT \leq t < nT + t_0)$$

$$I = 0 \quad (nT + t_0 \leq t < (n+1)T)$$

where, n being 0, 1, 2, 3 . . . .

Representing the central frequency by f, the induced voltage V, propagation time t and the transmission velocity V are given approximately as follows:
induced voltage V:

$$V = K \frac{d}{dt} (I_0(t - \Delta t) \exp(-\sqrt{\pi f \mu \sigma} \; d)$$

propagation time:

$$\Delta t = \sqrt{\frac{\mu \sigma}{4 \pi f}} \times d$$

where $\mu$ represents magnetic permeability, f represents frequency, $\sigma$ represents conductivity and d represents the thickness of the object to be examined.
transmission velocity $v$:

$$v = \sqrt{\frac{4 \pi f}{\mu \sigma}}$$

The velocity $v$ of transmission of the eddy currents is about 3 m/sec which is much smaller than the velocity of electromagnetic wave ($3 \times 10^8$ m/sec), on condition of $\mu = 150 \times 4\pi \times 10^{-7}$ H/m, $\sigma = 8 \times 10^6$ v/m and d=3 mm. The invention makes use of this fact. Namely, the signal transmitted through the object and the signal having detoured the object can be separated because the signal transmitted through the object lags by $\Delta t$ behind the signal which has detoured the object.

FIG. 7 shows an example of the transmitted pulse and an example of received pulse which varies as the transformation proceeds. On the other hand, the detouring signal is expressed as follows:

$$V = V_\epsilon(t) \quad (nT \leq t < nT + t_0)$$
$$= 0 \quad (nT + t_0 \leq t < (n+1)T)$$

Therefore, the influence of the detouring signal can be eliminated by picking up the signal consisting only of the component $nT + t_0 \leq t < (n+1)T$, in the signal processing performed by the signal processor 27 on the signal which has been received by the receiving coil 22 and amplified by the amplifier 26. Thus, the transmitted signal is separated from the detouring signal and the transformation degree is computed on the basis of the level of the transmitted signal and displayed on the display 28.

In the described measuring operation, either an A.C. current or a pulse current is used as the measuring electric current. As explained before, the use of an A.C. current suffers from a disadvantage in that there is a practical limit of the possibility of measurement in regard to the thickness of the object. On the other hand, in the case where a pulse current is used, the signal which has transmitted through the object exhibits a complicated waveform due to delay and attenuation of various frequency components of the FOURIER series constituting the signal, resulting in an inferior precision as compared with the case of measurement by continuous wave.

Therefore, when the occasion demands due to, for example, a too large thickness of the object, the measurement may be conducted by a method wherein the operation mode is switched by the pulse-continuous current change-over switch in such a manner that the A.C. current of a frequency which does not adversely affect the precision of measurement is used in the beginning period of the transformation, whereas, in the region in which the measurement cannot be conducted precisely with A.C. current, the pulse current is used as the measuring current in place of the A.C. current. The power amplifier provided at the input side of the transmission coil and the tuned amplifier and ordinary amplifier provided at the output side of the receiving coil are not essential for the constitution of the invention and, therefore, may be omitted, or be substituted by an equivalent. For instance, the tuned amplifier may be replaced with a lock-in amplifier.

By way of example, a description will be made hereinunder with specific reference to FIG. 8 as to application of the transformation degree sensor of the invention to a run-out table which is the cooling zone for cooling a strip after rolling by a hot strip mill.

Figure 8:
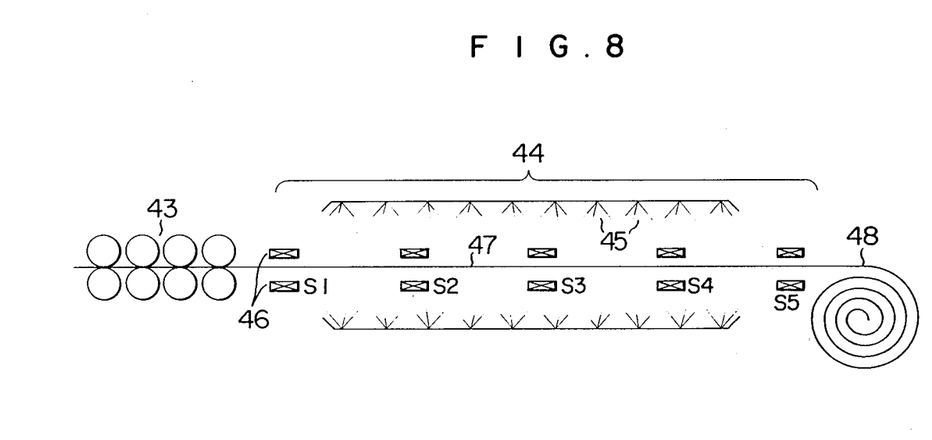
FIG. 8 is an illustration of a transformation degree sensor in accordance with the invention.

In FIG. 8, a reference numeral 43 denotes a finishing stand of a hot strip mill, 44 denotes a run-out table, 45 denotes cooling water, and 46S$_1$ to S$_5$ denote a series of sensor coils. Numerals 47 and 48 denote, respectively, a hot-rolled strip as the examination object and a coiler.

Figure 9:
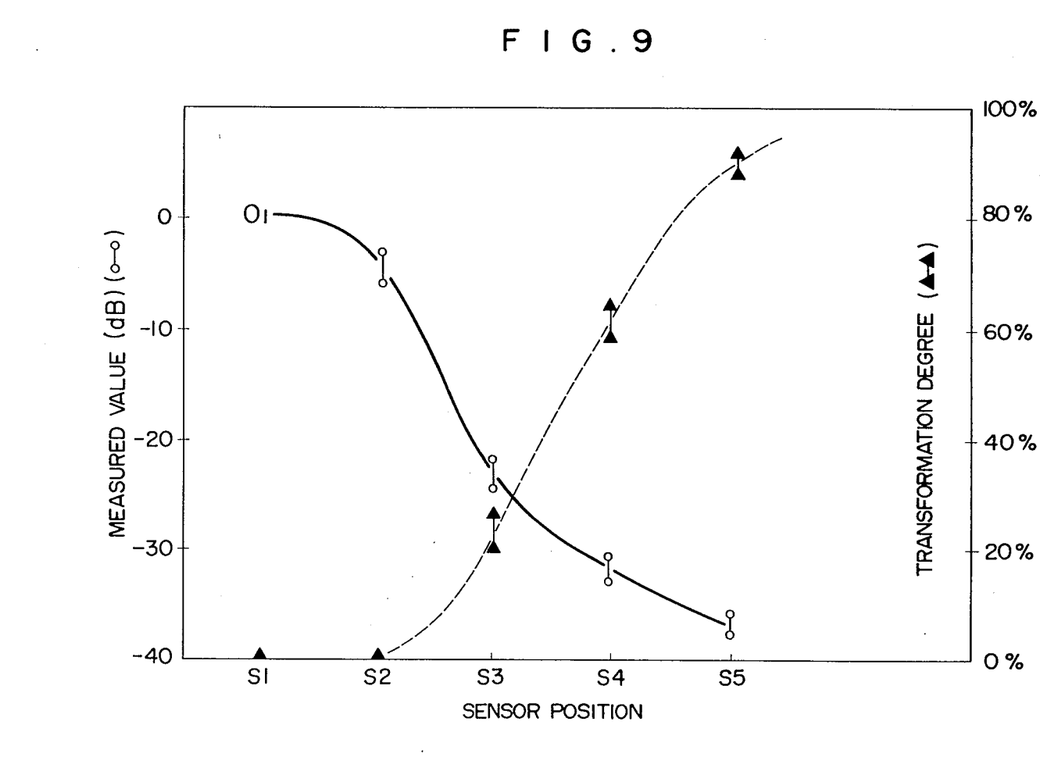
FIG. 9 is a graph showing the relationship between the output level and the transformation degree as obtained with different positions of the sensor shown in FIG. 8.

FIG. 9 shows the result of measurement. The hot-rolled strip is SM 50 as specified by JIS having a thickness of about 4 mm, and passes the run-out table at a speed of about 500 m/min. Using a continuous measuring current, the transformation degrees were measured by a plurality of sensors arranged along the run-out table. The outputs from respective sensors and the transformation degrees at respective sensor positions are shown by way of example.

In this application, an A.C. current having sine-waveform and a frequency of 500 Hz was used over the entire region of transformation from 0% to 100%. The distance between the transmission coil and the receiving coil was selected to be 300 mm, and the strip as the measuring object was made to pass through the gap between these coils. The pitch of the transmission/receiving coils was constant. In the illustrated case, the distance between S$_1$ and S$_2$ is 30 m.

A shield plate as shown in FIG. 4 was used in this application. Although a multiplicity of sensors are used, the number of the sensors is not critical.

It is even possible to effect the control of, for example, cooling of the hot-rolled strip by a single sensor provided on the run-out table.

In this application in which the object has a small thickness of about 4 mm, the measurement could be conducted satisfactorily over the entire range of transformation from 0% to 100% by using an A.C. current as the measuring current.

A test measurement was conducted in which the transformation degree in a steel sheet of 5 mm thick was measured by switching the measuring mode from the A.C. current measuring mode to the pulse current measuring mode at a degree of transformation ranging between 50 and 70%.

The peak-to-peak voltage of this pulse current was 10 V, while the pulse width and frequency were 1 msec and 10 msec, respectively.

What is claimed is:

1. A method of measuring the degree of transformation of the structure of an object comprising:
   placing said object between a transmission coil and a receiving coil, said receiving coil being shielded by a shield plate and a shield cup made of a material having a large magnetic permeability for exposing only the portion of said receiving coil facing said transmission coil;
   supplying said transmission coil with a pulse current through an oscillator and a first amplifier; and
   detecting the degree of transformation by means of an electric signal obtained through said receiving coil, said electric signal being independent of the distance between said receiving coil and said object, said electric signal being converted by a second amplifier and a signal processor into a highly precise degree of transformation.

2. A method of measuring the degree of transformation of the structure of an object having a certain thickness, comprising:
   placing said object between a single transmission coil and a single receiving coil;
   supplying said transmission coil with an electric current through an oscillator and a first amplifier; and
   detecting the degree of transformation by means of an electric signal obtained through said receiving coil, said receiving coil being shielded by a shield plate and a shield cup made of a material having a large magnetic permeability for exposing only the portion of the receiving coil facing said transmission coil, said electric signal obtained from said receiving coil being converted by a second amplifier and a signal processor into the transformation degree;
   wherein said electric current applied to said transmission coil is an A.C. electric current in the beginning part of the transformation period and wherein, after the transformation has proceeded to a predetermined degree, said electric current supplied to said transmission coil is a pulse current;
   whereby, irrespective of the thickness of the object, a precise degree of transformation is detected.

3. A method of measuring the degree of transformation of the structure of a metallic material under varying temperature-time relation, said method comprising:
   moving said metallic material along a path defined between a transmission coil and a receiving coil;
   supplying said transmission coil with an A.C. current through an oscillator and a first amplifier; and
   detecting the degree of transformation by means of an electric signal obtained through said receiving coil, said receiving coil being shielded by a shield plate and a shield cup made of a material having a large magnetic permeability for exposing only the portion of the receiving coil facing said transmission coil;
   wherein said electric signal obtained is independent of the distance between said receiving coil and said metallic material, said electric signal obtained from said receiving coil being converted by a second amplifier and a signal processor into a highly precise degree of transformation.

4. A method of measuring the degree of transformation of the structure of an object according to any one of claims 1, 2 or 3, wherein the frequency f of a continuous wave electric current is determined to meet the following conditions in relation to the thickness d, magnetic permeability $\mu$, conductivity $\sigma$ and a factor $K_0$ determined by the shape of the measuring system, whereby the measurement is conducted over the whole period from the beginning till the end of the transformation:

$$f \leq K_0/d^2\mu\sigma$$

5. A method of measuring the degree of transformation of a structure of an object according to any one of claims 1, 2, or 3, further comprising: covering said receiving coil by a shield plate and a shield cup in such a manner that only the face of said receiving coil facing said transmission coil is exposed, thereby excluding signal which may reach said receiving coil detouring said object.

* * * * *